United States Patent [19]

Baumann et al.

[11] 4,250,101

[45] Feb. 10, 1981

[54] BIS-EPOXY-DIALKOXY-ALKANES

[75] Inventors: Manfred Baumann, Mannheim; Werner Hoffmann, Neuhofen, both of Fed. Rep. of Germany

[73] Assignee: BASF Aktiengesellschaft, Fed. Rep. of Germany

[21] Appl. No.: 54,863

[22] Filed: Jul. 5, 1979

[30] Foreign Application Priority Data

Jul. 19, 1978 [DE] Fed. Rep. of Germany ....... 2831676

[51] Int. Cl.³ ............................................. C07D 303/22
[52] U.S. Cl. ............................... 260/348.57; 260/347.8
[58] Field of Search ....................... 260/348.57, 348.17

[56] References Cited

U.S. PATENT DOCUMENTS

| | | | |
|---|---|---|---|
| 3,171,858 | 3/1965 | L'Italien | 260/348.17 |
| 3,492,351 | 1/1970 | Koppe et al. | 260/348.17 |
| 3,558,714 | 1/1971 | Buchi et al. | 260/594 |
| 3,629,292 | 12/1971 | Evers | 260/347.8 |
| 3,694,466 | 9/1972 | Buchi et al. | 260/347.8 |
| 3,728,397 | 4/1973 | Re et al. | 260/594 |
| 3,887,589 | 6/1975 | Eykelboom et al. | 260/347.8 |

FOREIGN PATENT DOCUMENTS

| | | |
|---|---|---|
| 1915788 | 10/1969 | Fed. Rep. of Germany . |
| 1768649 | 12/1972 | Fed. Rep. of Germany . |
| 2105014 | 3/1973 | Fed. Rep. of Germany . |
| 2359891 | 6/1974 | Fed. Rep. of Germany . |
| 1440270 | 6/1976 | United Kingdom . |

OTHER PUBLICATIONS

George Buchi et al., J. Org. Chem., vol. 38, No. 1, (1973), pp. 123–125.

Current Abstracts of Chemistry, vol. 37, Issue 331, (1970), 135034.

A. Weissberger, Heterocyclic Compounds with Three- and Four-Membered Rings, Part One, (1964), pp. 137–139.

Calvin L. Stevens et al., Jour. Am. Chem. Soc., vol. 76, (1954), pp. 718–720.

V. S. Karavan et al., Zhurnal Organ. Khimii, vol. 3, No. 11, Nov. 1967, pp. 1983–1987.

V. N. Yandoviskii et al., Zhurnal Organ. Khimii, vol. 4, No. 10, pp. 1758–1764, Oct. 1968.

*Primary Examiner*—Norma S. Milestone
*Attorney, Agent, or Firm*—Keil & Witherspoon

[57] ABSTRACT

Bis-epoxy-dialkoxy-alkanes are valuable intermediates for the preparation of the sought-after aromatic 2,5-dimethyl-4-hydroxy-2,3-dihydrofuran-3-one. The novel bis-epoxy-dialkoxy-alkanes are obtained by reacting the corresponding $\alpha,\alpha'$-dihalo-1,2-diketones with an alkali metal hydroxide or an alkali metal alkoxide and an alkanol at from $-20°$ to $+100°$ C. To prepare the 2,5-dialkyl-4-hydroxy-2,3-dihydro-furan-3-ones, which are valuable aromatics, the novel bis-epoxy-dialkoxy-alkanes are heated with strong mineral acids or strong organic acids at from $60°$ to $120°$ C.

3 Claims, No Drawings

BIS-EPOXY-DIALKOXY-ALKANES

The present invention relates to the novel bis-epoxy-dialkoxy-alkanes of the general formula I

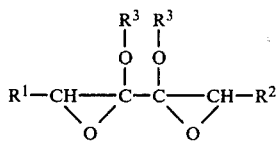

where $R^1$, $R^2$ and $R^3$ are alkyl of 1 to 4 carbon atoms, preferably methyl or ethyl, to a process for their preparation and to their use for the preparation of aromatics of the general formula III

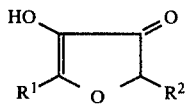

where $R^1$ and $R^2$ have the above meanings, in particular the preparation of the sought-after aromatic 2,5-dimethyl-4-hydroxy-2,3-dihydro-furan-3-one of the formula IIIa

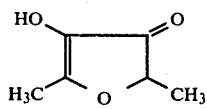

The novel bis-epoxy-dialkoxy-alkanes cannot themselves be used as scents but are of particular importance as valuable intermediates for the preparation of the aromatics of the formula III, especially of the aromatic of the formula IIIa.

Numerous processes have been proposed for the synthesis of the natural fruit aromatic of the formula IIIa, a compound encountered in pineapples and strawberries, but these processes are unsatisfactory for various reasons and cannot be economically scaled up to industrial operation.

For example, according to Büchi and Demole (J. Org. Chem., 38 (1973), pages 123 et seq.), 2,5-dimethyl-furanone is used as the starting material and is converted by bromination in methanol solution into 2,5-dimethyl-2,5-dimethoxy-2,5-dihydrofuran, and the latter is oxidized with potassium chlorate in the presence of a catalytic amount of osmium tetroxide to give 3,4-dihydroxy-hexane-2,5-dione, which can be cyclized in the presence of bases to give the compound IIIa. This synthesis is involved and requires the use of potassium chlorate, which presents some problems, and of osmium tetroxide, which is expensive and toxic, so that the process is unsuitable for industrial operation.

A variant of this process, described by the same authors (loc. cit.), which differs merely in that 3,4-dihydroxy-hexane-2,5-dione is prepared by another method, namely by hydrodimerization of methylglyoxal in the presence of zinc dust, is also unsatisfactory. The last-mentioned reaction, which consists of a plurality of component operations, is technologically difficult to control in the case of sizable batches, and furthermore gives yields of only about 20%.

The process of German Pat. No. 2,105,014, in which 2,5-dihalo-hexane-3,4-diones are cyclized with aqueous alkali to give compound IIIa is also not entirely satisfactory, since the yields obtained are only about 30%.

In a similar process (German Laid-Open Application DOS No. 1,768,649), 2,5-dihydroxy-hexane-3,4-dione is converted to IIIa. Since, however, this diol-dione can for its part only be prepared by ozonization of 2,5-dihydroxy-hex-3-yne, a reaction which is hazardous and technically difficult to control, this process for the preparation of IIIa can again not be realized industrially without great difficulties.

Instead of the diol-diones, their esters, such as the diacetates, have also been employed for cyclization to give IIIa (cf. German Laid-Open Application DOS No. 1,915,788). However, these esters are prepared via a Grignard reaction and an oxidation with potassium permanganates, and these are process steps which are known to require precise observance of quite specific reaction conditions; as a result, an industrial synthesis employing these esters is cumbersome and expensive.

In a further process (German Laid-Open Application DOS No. 2,359,891), which comprises condensation of a sodium derivative of an acetoacetic acid ester with α-bromo-propionyl chloride, followed by decarboxylation and oxidation, the yields achieved are only about 15%, based on the bromo-propionyl chloride.

It is an object of the present invention to provide novel methods and novel starting compounds by means of which the sought-after aromatic IIIa can be prepared more economically and technologically more simply than hitherto.

We have found that this object is achieved with bis-epoxy-dialkoxy-alkanes of the general formula I

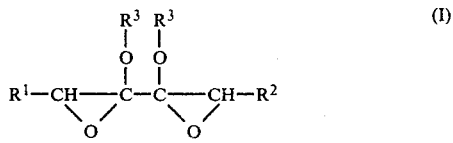

where $R^1$, $R^2$ and $R^3$ are alkyl of 1 to 4 carbon atoms, preferably methyl or ethyl, especially methyl, these being novel compounds which on the one hand can be prepared relatively simply in good yields and on the other hand can, by heating with strong acids, be converted simply and in relatively good yields to the compound IIIa or more generally to the aromatics III.

Accordingly, the present invention relates to the novel bis-epoxy-dialkoxy-alkanes of the formula I and to a process for the preparation of the said compounds, wherein α,α'-dihalo-1,2-diketones of the general formula II

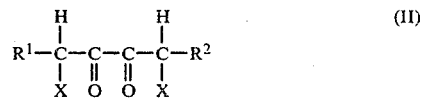

where $R^1$ and $R^2$ have the above meanings and X is Cl or Br, are reacted with an alkali metal hydroxide or an alkali metal alkoxide of the formula $R^3$—O—Me, where Me is K, Na or Li, preferably Na, and an alcohol of the formula $R^3$—OH, at from $-20°$ to $+100°$ C., preferably from 0° to 25° C.

The invention further relates to the use of the novel bis-epoxy-dialkoxy-alkanes of the general formula I for the preparation of aromatics of the general formula III

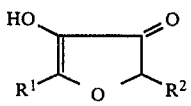
(III)

where $R^1$ and $R^2$ have the above meanings, by heating with strong mineral acids or strong organic acids at from 60° to 120° C.

The α,α'-dihalo-1,2-diketone starting compounds, of the general formula II, can be prepared by a relatively simple conventional method, namely halogenation of the corresponding diketones with an approximately stoichiometric amount of the particular halogen under acid conditions.

Suitable alkali metal hydroxides are KOH, NaOH and LiOH, preferably NaOH.

Suitable alkali metal alkoxides are potassium, sodium or lithium alkoxides of 1 to 4 carbon atoms, preferably sodium alkoxides, especially sodium methylate.

The alkali metal hydroxides and alkali metal alkoxides are in general used in amounts of from 2 to 4 moles, preferably from 2 to 2.5 moles, per mole of dihalide.

Suitable alkanols are those of 1 to 4 carbon atoms, eg. methanol, ethanol, propanol, isopropanol, n-butanol and isobutanol, especially methanol.

If alkali metal alkoxides are used, it is advantageous to employ the same alkanol as that on which the alkali metal alkoxide is based.

The alkanol is in general used in an amount of from 5 to 20 moles per mole of dihalide, ie. the alkanol also serves as the solvent. For example, the reaction is carried out in a solution, of from about 10 to 30% strength, of the alkali metal hydroxide or alkali metal alkoxide. If concentrated solutions are used, precipitation of salts can make stirring difficult.

The reaction temperature can be from −20° to about +100° C., preferably from 0° to 25° C.

The reaction time is in general from 2 to 24 hours, preferably from 3 to 6 hours.

The reaction procedure is advantageously to dissolve the alkali metal hydroxide or an alkali metal in the alkanol and to add slowly to the resulting solution (or, in the case of LiOH, suspension) of the alkali metal hydroxide or alkali metal alkoxide, at the reaction temperature, a solution of the dihalide of the formula II in the corresponding alkanol, after which the reaction mixture is left, for the remainder of the reaction time, at room temperature, or at the reaction temperature, whilst stirring. It is also possible to add the solution of the alkali metal hydroxide or alkali metal alkoxide to the solution of the dihalide in the alkanol, but in this variant the yields obtained are somewhat lower.

The bis-epoxy-dialkoxy-alkanes are isolated in the conventional manner, for example by filtering off the salt formed during the reaction, concentrating the alcoholic solution and then distilling the residue, or alternatively by concentrating the reaction mixture, taking up the residue in a water-immiscible solvent, such as ether, chloroform, ethyl acetate or the like, washing out the salt formed during the reaction, drying the organic solution, concentrating it and then distilling the residue.

However, to prepare the aromatics of the formula III, the bis-epoxy-dialkoxy-alkanes are advantageously used directly in the form of the crude product obtained, for example, by filtering and concentrating the reaction mixture after completion of the reaction.

Any conventional strong acid having a dissociation constant (in water, at 25° C.) greater than about $10^{-4}$ can be used to cyclize the bis-epoxy-dialkoxy-alkanes to give the aromatics of the formula III. Preferred strong acids are inorganic acids, eg. sulfuric acid, hydrochloric acid, perchloric acid, hydrobromic acid, hydriodic acid, phosphoric acid and the like. Strong organic acids, eg. formic acid, oxalic acid, trichloroacetic acid and the sulfonic acids, are also preferred. Amongst the strong acids mentioned above, the relatively cheap strong inorganic acids, eg. sulfuric acid and phosphoric acid, and the relatively non-corrosive strong organic acids, eg. oxalic acid and p-toluenesulfonic acid, are preferred for the process according to the invention.

The cyclization is carried out in water or in a mixture of water with a hydrophilic solvent, for example in a mixture of water with methanol or ethanol, dioxane, tetrahydrofuran or dimethoxyethane. Preferred solvents are pure water, and mixtures of methanol or ethanol with water.

The reaction temperatures are from 60° to 120° C., preferably from 80° to 100° C. and the reaction time is from 1 to 12 hours, depending on the temperature and on the amount of acid.

The aromatics III are isolated in the conventional manner, for example by extraction with a water-immiscible or only slightly water-miscible solvent, drying and concentrating the extract, and subsequently distilling or subliming the residue.

The bis-epoxy-dialkoxy-alkanes according to the invention provide a surprisingly advantageous method of synthesizing the sought-after aromatic of the formula IIIa and of corresponding higher alkyl-substituted compounds having very good organoleptic properties.

EXAMPLE 1

A solution of 32 g (0.175 mole) of 2,5-dichlorohexane-3,4-dione in 50 ml of methanol was added dropwise in the course of 6 minutes to 80 g of a 30% strength NaOCH$_3$ solution (0.44 mole) at from 15° to 20° C. (ie. with slight cooling). The reaction mixture was then stirred for a further 24 hours at room temperature.

To work up the reaction mixture, the methanol was stripped off, the residue was taken up in ether and the salts formed were then washed out with water. The ether solution was dried and concentrated. 17.3 g remained, corresponding to a crude yield of 57% of theory. A sample was distilled. The novel compound 2,3;4,5-bis-epoxy-3,4-dimethoxy-hexane has a boiling point of 25°–30° C./0.05 mbar and a refractive index $n_D^{25}$ of 1.4366.

The structure is confirmed by the IR spectrum and NMR spectrum, and by analysis. The product is a diastereomer mixture.

EXAMPLE 2

A solution of 55 g (0.2 mole) of 2,5-dibromo-hexane-3,4-dione in 100 ml of methanol was added dropwise in the course of 2 hours to 90 g of a 30% strength NaOCH$_3$ solution (0.5 mole) at 0°–5° C. The reaction mixture was then stirred for 20 hours at 0° C.

On working up by a method similar to that of Example 1, 35.5 g of crude 2,3;4,5-bis-epoxy-3,4-dimethoxy-hexane remained (corresponding to 100% crude yield).

EXAMPLE 3

A solution of 55 g (0.2 mole) of 2,5-dibromo-hexane-3,4-dione in 100 ml of methanol was added dropwise in the course of 2 hours to 90 g of a 30% strength NaOCH$_3$ solution, whilst heating under reflux. The reaction mixture was then refluxed for a further 3 hours.

On working up by a method similar to that of Example 1, 2,3;4,5-bis-epoxy-3,4-dimethoxy-hexane was obtained in a crude yield of 70%.

EXAMPLE 4

A solution of 55 g (0.2 mole) of 2,5-dibromo-hexane-3,4-dione in 100 ml of methanol was added dropwise in the course of 2 hours to 90 g of a 30% strength NaOCH$_3$ solution (0.5 mole) at from about 15° to 20° C., and the reaction mixture was then stirred for 3 hours at the same temperature. On working up by a method similar to that of Example 1, 2,3;4,5-bis-epoxy-dimethoxy-hexane was obtained in a crude yield of 91%.

EXAMPLE 5

5 g (0.22 mole) of Na were converted by means of 110 ml of ethanol into an Na ethylate solution, to which a solution of 27.2 g (0.1 mole) of 2,5-dibromo-hexane-3,4-dione in 50 ml of ethanol was added in the course of 30 minutes at 15°-20° C. The reaction mixture was then stirred for 16 hours at room temperature, and was worked up by a method similar to that of Example 1. 14.9 g of crude product were obtained, distillation of which gave 11.5 g (corresponding to a yield of 57% of theory) of 2,3;4,5-bis-epoxy-diethoxy-hexane having a boiling point of 38°-39° C./0.05 mbar and a refractive index n$_D^{25}$ of 1.4248.

The structure is confirmed by the IR spectrum and NMR spectrum and by analyses.

EXAMPLE 6

A potassium isobutylate solution was prepared from 8.9 g (0.22 mole) of potassium and 150 ml of isobutanol. A solution of 27.2 g (0.1 mole) of 2,5-dibromo-hexane-3,4-dione in 100 ml of isobutanol was added dropwise thereto in the course of 30 minutes at 15°-20° C., and the reaction mixture was then stirred for 20 hours at room temperature, and worked up by a method similar to that of Example 1. 20.8 g of crude product remained; its IR spectrum and NMR spectrum support the assumed structure. On attempting to distil this product, decomposition occurred.

EXAMPLE 7

(a) 40 g (0.74 mole) of KOH were converted by means of 200 ml of methanol into a K methylate solution, to which a solution of 82 g (0.3 mole) of 2,5-dibromo-hexane-3,4-dione in 100 ml of methanol was added at 15°-20° C. in the course of 60 minutes. The reaction mixture was then stirred for 4 hours at 20° C.

It was then filtered and concentrated, the residue was taken up in ether, the salts were washed out and the ether solution was dried and concentrated. 34 g of residue remained; according to the IR spectrum and NMR spectrum, this material contained, in addition to the compound obtained in Example 1, about 15% of a substance in which the epoxy-ether had been opened to give the α-hydroxycarbonyl compound.

(b) On following the procedure described in Example 7(a), but using 29.5 g (0.74 mole) of NaOH in 300 ml of methanol instead of 40 g (0.74 mole) of KOH in 200 ml of methanol, 24 g of a residue identical with the substance obtained according to Example 1 remained.

(c) On following the procedure described in Example 7(a), but using 20 g (0.74 mole) of LiOH instead of 40 g (0.74 mole) of KOH, 14.4 g of a residue having the same spectrum as the residue obtained according to 7(a) remained.

EXAMPLE 8

A solution of 55 g (0.192 mole) of 2,5-dibromo-heptane-3,4-dione in 30 ml of methanol was added dropwise in the course of 6 minutes to a solution containing 0.416 mole of NaOCH$_3$ in 100 ml of methanol, at 15°-20° C. The reaction mixture was then stirred for 16 hours.

On working up the reaction mixture by a method similar to that of Example 1, 22.4 g of a residue were obtained. Subsequent distillation of this crude product gave 17 g (corresponding to a yield of 47% of theory) of 2,3;4,5-bis-epoxy-3,4-dimethoxy-heptane having a boiling point of 40°-42° C./0.2 mbar and a refractive index n$_D^{25}$ of 1.4293. The IR and NMR spectroscopy data confirmed the structure.

EXAMPLE 9

(a) 31 g (0.178 mole) of crude 2,3;4,5-bis-epoxy-3,4-dimethoxy-hexane obtained according to Example 1 were added dropwise in the course of 90 minutes, under an N$_2$ atmosphere, to 70 ml of refluxing 5% strength aqueous H$_2$SO$_4$, after which the reaction mixture was refluxed for 3 hours. After it had been cooled, it was neutralized with concentrated sodium carbonate solution and extracted with ethyl acetate, and the organic phase was dried and concentrated. 21.3 g of residue remained. On subsequent distillation, 10.3 g of (IIIa) were obtained, and proved identical with (IIIa) prepared by other methods. Melting point 68°-70° C. The yield of (IIIa), namely 2,5-dimethyl-4-hydroxy-2,3-dihydro-furan-3-one, was 45% of theory, based on crude 2,3;4,5-bis-epoxy-3,4-dimethoxy-hexane employed.

(b) On following the procedure described in Example 9(a), but using a solution of 15 g of oxalic acid dihydrate in 400 ml of water instead of using 70 ml of 5% strength aqueous sulfuric acid, the compound IIIa was obtained in about the same yield.

(c) On following the procedure described in Example 9(a), but using the 2,3;4,5-bis-epoxy-3,4-diethoxy-hexane obtained according to Example 5 in place of crude 2,3;4,5-bis-epoxy-3,4-dimethoxy-hexane, the compound IIIa was obtained in about the same yield as in Example 9(a).

EXAMPLE 10

15.5 g of crude 2,3;4,5-bis-epoxy-3,4-dimethoxy-heptane obtained as described in Example 8 were added dropwise in the course of 2 hours, under an N$_2$ atmosphere, to 100 ml of refluxing 5% strength aqueous H$_2$SO$_4$, after which the reaction mixture was refluxed for 3 hours. On working up the reaction mixture by a method similar to that of Example 9(a), 9.1 g of crude product were obtained. Distillation gave 5.6 g (corresponding to 48% of theory) of a mixture of about 25% of 2-methyl-5-ethyl-4-hydroxy-2,3-dihydro-furan-3-one and about 75% of 5-methyl-2-ethyl-4-hydroxy-2,3-dihydro-furan-3-one, having a boiling point of 89°-91° C./0.1 mbar.

EXAMPLE 11

A solution of 60 g (0.2 mole) of 2,5-dibromo-octane-3,4-dione in 100 ml of methanol was added dropwise in the course of 2 hours to 90 g of a 30% strength NaOCH₃ solution (0.5 mole) at 0°–5° C. The reaction mixture was then stirred for 20 hours at 0° C.

On working up by a method similar to Example 1, 2,3;4,5-bis-epoxy-3,4-dimethoxy-octane was obtained in 70% yield. The product had a boiling point of 51°–52° C./0.1 mbar and a refractive index $n_D^{25}$ of 1.4310.

EXAMPLE 12

On following the procedure described in Example 11, but using 63 g (0.2 mole) of 2,5-dibromo-nonane-3,4-dione instead of 60 g of 2,5-dibromo-octane-3,4-dione, 2,3;4,5-bis-epoxy-3,4-dimethoxy-nonane, having a boiling point of 61°–63° C./0.1 mbar and a refractive index $n_D^{25}$ of 1.4334 was obtained in 71% yield.

EXAMPLE 13

On following the procedure described in Example 11, but using 60 g of 2,5-dibromo-6-methyl-heptane-3,4-dione instead of 60 g of 2,5-dibromo-octane-3,4-dione, 2,3;4,5-bis-epoxy-3,4-dimethoxy-6-methyl-heptane, having a boiling point of 36° C./0.01 mbar and a refractive index $n_D^{25}$ of 1.4257 was obtained in 47% yield.

EXAMPLE 14

On following the procedure described in Example 11, but using 63 g of 2,5-dibromo-7-methyl-octane-3,4-dione instead of 60 g of 2,5-dibromo-octane-3,4-dione, 2,3;4,5-bis-epoxy-3,4-dimethoxy-7-methyl-octane, having a boiling point of 50° C./0.05 mbar and a refractive index $n_D^{25}$ of 1.4324 was obtained in 58% yield.

EXAMPLE 15

13 g (0.064 mole) of the 2,3;4,5-bis-epoxy-3,4-dimethoxy-octane obtained according to Example 11 were reacted, by a method similar to that of Example 9(a), with 70 ml of 5% strength aqueous H₂SO₄. This gave a 1:1 mixture of 2-methyl-5-propyl- and 2-propyl-5-methyl-4-hydroxy-2,3-dihydro-furan-3-one in 48% yield, the mixture having a boiling point of 85°–95° C./0.1 mbar.

EXAMPLE 16

15 g (0.07 mole) of the 2,3;4,5-bis-epoxy-3,4-dimethoxy-nonane obtained according to Example 12 were reacted with 70 ml of 5% strength aqueous H₂SO₄ by a method similar to that of Example 9(a). This gave a 1:1 mixture of 2-methyl-5-butyl- and 2-butyl-5-methyl-4-hydroxy-2,3-dihydro-furan-3-one, in 44% yield. The mixture had a boiling point of 101°–105° C./0.1 mbar.

EXAMPLE 17

9.5 g (0.047 mole) of 2,3;4,5-bis-epoxy-3,4-dimethoxy-6-methyl-heptane, obtained according to Example 13, were reacted with 70 ml of 5% strength aqueous H₂SO₄ by a method similar to that of Example 9(a). This gave 2-isopropyl-5-methyl-4-hydroxy-2,3-dihydro-furan-3-one, having a boiling point of 120° C./0.01 mbar, in 35% yield.

EXAMPLE 18

12 g (0.056 mole) of 2,3;4,5-bis-epoxy-3,4-dimethoxy-7-methyl-octane obtained according to Example 14 were reacted with 70 ml of 5% strength aqueous H₂SO₄ by a method similar to that of Example 9(a). This gave a mixture of 2-methyl-5-isobutyl-and 2-isobutyl-5-methyl-4-hydroxy-2,3-dihydro-furan-3-one in 58% yield. The mixture had a boiling point of 145°–150° C./0.1 mbar and a refractive index $n_D^{20}$ of 1.4337.

We claim:
1. A bis-epoxy-dialkoxy-alkane of the general formula I

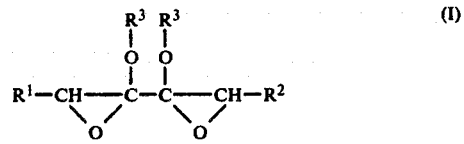

where R¹, R² and R³ are alkyl of 1 to 4 carbon atoms.
2. A compound as set forth in claim 1 wherein R¹, R² and R³ are each methyl.
3. A compound as set forth in claim 1 wherein R¹, R² and R³ are methyl or ethyl.

* * * * *